United States Patent [19]

Trotta et al.

[11] Patent Number: 5,391,706
[45] Date of Patent: Feb. 21, 1995

[54] PURIFICATION OF GM-CSF

[75] Inventors: Paul P. Trotta, Rutherford; Gail F. Seelig, Watchung; Robert A. Kosecki, Flemington; Paul Reichert, Montville, all of N.J.

[73] Assignee: Schering Plough Corporation, Madison, N.J.

[21] Appl. No.: 125,356

[22] Filed: Sep. 21, 1993

Related U.S. Application Data

[63] Continuation of Ser. No. 870,153, Apr. 14, 1992, abandoned, which is a continuation of Ser. No. 455,453, Dec. 15, 1989, abandoned, which is a continuation-in-part of Ser. No. 74,410, Jul. 16, 1987, abandoned.

[51] Int. Cl.$^6$ .............................................. C07K 3/20
[52] U.S. Cl. .................................... 530/351; 530/397; 530/416; 530/417; 435/69.5
[58] Field of Search ................. 435/69.1, 69.5, 172.3; 530/351, 397, 399, 412, 415, 416, 417

[56] References Cited

U.S. PATENT DOCUMENTS

| | | | |
|---|---|---|---|
| 4,438,032 | 3/1984 | Golde et al. | 435/240.1 |
| 4,658,018 | 4/1987 | Urdal et al. | 530/351 |
| 5,078,996 | 1/1992 | Conlon, III et al. | 424/85.1 |

FOREIGN PATENT DOCUMENTS

| | | | |
|---|---|---|---|
| 0118915 | 9/1984 | European Pat. Off. | 435/240.1 |
| 0183198 | 6/1986 | European Pat. Off. | 435/69.1 |
| 0215126 | 3/1987 | European Pat. Off. | 435/69.1 |
| 0041615 | of 1983 | Japan | 530/351 |
| 8600639 | 1/1986 | WIPO | 435/69.1 |
| 8604067 | 7/1986 | WIPO | 435/69.1 |

OTHER PUBLICATIONS

Nicola "Methods of Enzymology", 116, 600–619 (1985).
Onoue, et al., Biochimica et Biophysica Acta 881, 437–445 (1986).
Pharmacia Fine Chemicals (A) "Group Specific Adsorbents", Affinity Chromatography, 47–82 (1983).
Pharmacia Fine Chemicals (B), "Experimental Technique I", Ion Exchange Chromatography, 27–38 (1983).
Wong et al., Science, 228, 810–815 (1985).
Gasson et al., Science, 226, 1339–42 (1984).
Stanley et al., J. Biol. Chem. 252(12), 4035–12 (1977).
Sparrow, et al., Proc. Natl. Acad. Sci. USA 82 292–96 (1985).
Waheed et al., Blood, 60(1), 238–244 (1982).
Shadduck, et al., Blood 53(6), 1182–1190 (1979).
Shadduck et al., Proc. Soc. Exp. Biol. Med. 164, 40–50 (1980).
Gianazza et al., Biochem J. 201:129–136 (1982).

*Primary Examiner*—Margaret Parr
*Assistant Examiner*—Scott W. Houtteman
*Attorney, Agent, or Firm*—Paul Lunn; Gerald Rosen; Norman Dulak

[57] ABSTRACT

A method of purifying granulocyte-macrophage colony-stimulating factor (GM-CSF), particularly recombinant human GM-CSF, in good yield and with retention of biological activity, comprising sequential anion-exchange, dye-ligand affinity, gel filtration and reversed-phase chromatography is disclosed.

6 Claims, No Drawings

PURIFICATION OF GM-CSF

The present application is a continuation of U.S. application Ser. No. 07/870,153, filed Apr. 14, 1992, which is now abandoned, which is a continuation of U.S. application Ser. No. 07/455,453, filed Dec. 15, 1989, and is now abandoned, which is the United States national application corresponding to International Application No. PCT/US88/02294, filed Jul. 13, 1988 and designating the United States, which PCT application is in turn a continuation-in-part of U.S. application Ser. No. 074,410, filed Jul. 16, 1987, which is now abandoned, the benefit of which applications is claimed pursuant to the provisions of 35 U.S.C. §120,363, and 365 (c).

SUMMARY OF THE INVENTION

The present invention relates to a method for purifying granulocyte-macrophage colony-stimulating factor (GM-CSF), particularly human GM-CSF.

The detection, isolation and purification of these factors is extremely difficult, for it is frequently complicated by the nature of the supernatants in which they are typically located, the divergencies and cross-overs of activities of the various components in the mixtures, the sensitivity (or lack thereof) of the assays utilized to ascertain the factors' properties, the frequent similarity in the range of molecular weights and other characteristics of the factors, and the very low concentration of the factors in their natural settings.

The method of this invention provides for a particular series of purification steps which result in GM-CSF with high specific biological activity, high electrophoretic purity and a low level of pyrogens or other contaminants.

BACKGROUND

Circulating blood cells are constantly replaced by newly developed cells. Replacement blood-cells are formed in a process termed hematopoiesis, in which at least eight mature blood cell lineages are produced: red blood cells (erythrocytes), macrophages (monocytes), eosinophilic granulocytes, megakaryocytes (platelets), neutrophilic granulocytes, basophilic granulocytes (mast cells), T lymphocytes, and B lymphocytes [see Burgess and Nicola, *Growth Factors and Stem Cells* (Academic Press, New York, 1983)]. Much of the control of blood cell formation is mediated by a group of interacting glycoproteins termed colony stimulating factors (CSFs). These glycoproteins are so named because of the in vivo and in vitro assays used to detect their presence. Techniques for the clonal culture of hematopoietic cells in semisolid culture medium have been especially important in the development of in vitro assays. In such cultures, individual progenitor cells (i.e., cells developmentally committed to a particular lineage, but still capable of proliferation) are able to proliferate to form a colony of maturing progeny in a manner which is believed to be essentially identical to the comparable process in vivo.

As more CSFs become available, primarily through molecular cloning, interest has heightened in finding clinical applications for them. Their use has been suggested for several clinical situations where the stimulation of blood cell generation would be desirable, such as for rehabilitative therapy after chemotherapy or radiation therapy of tumors, treatment of myeloid hypoplasias, treatment of neutrophil deficiency, treatment to enhance hematopoietic regeneration following bone marrow transplantation, and treatment to increase host resistance to established infections.

Complementary DNAs (cDNAs) for GM-CSF, factors which support growth and development of granulocytes and macrophages, have recently been cloned and sequenced by a number of laboratories. Moreover, non-recombinant GM-CSF has been purified from culture supernatants of the Mo cell line (described in U.S. Pat. No. 4,438,032), and the first sixteen amino acids from the N-terminus have been sequenced [Gasson et al., *Science*, Vol. 226, pgs. 1339–1342 (1984)]. Among the human GM-CSFs, heterogeneity of the nucleotide sequence and amino acid sequence has been observed. For example, at the amino acid level both threonine and isoleucine have been observed at position 100 with respect to the N-terminal alanine, suggesting that several allelic forms, or polymorphs, of GM-CSF may exist within human populations.

A variety of methods are now available for de novo preparation and cloning of cDNAs, and for the construction of cDNA libraries.

By way of example, total mRNA is extracted from cells (e.g., a nontransformed human T cell source) producing polypeptides exhibiting the desired activity. The double-stranded cDNAs can be constructed from this total mRNA by using primer-initiated reverse transcription to make first the complement of each mRNA sequence, and then by priming for second strand synthesis. Subsequently, the cDNAs can be cloned by joining them to suitable plasmids or bacteriophage vectors through complementary homopolymeric tails or cohesive ends created with linker segments containing appropriate restriction sites, and then transforming a suitable host. A wide range of expression systems (i.e., host/expression-vector combinations) can be used to produce the proteins purified by the process of this invention. Possible types of host cells include, but are not limited to, bacterial, yeast, insect, mammalian and the like.

Various methods have been disclosed for extracting the GM-CSF from the host cells and subsequently purifying it, but GM-CSF is not always adequately purified in good yield and with retention of biological activity.

DETAILED DESCRIPTION

The present invention comprises a unique series of chromatographic steps which purify GM-CSF to more than 95% homogeneity, with the retention of biological activity, and in good yield.

The procedure is composed of sequential anion-exchange, dye-ligand affinity, gel filtration and reversed-phase chromatography.

The anion exchange column is used to remove proteases from the supernatant obtained after the host cells are killed and filtered off. Quaternary aminoethyl, mixed amine or other intermediate base resins or weak base resins such as p-amino benzyl cellulose are particularly useful. Quaternary aminoethyl is a preferred anion exchange resin. The quaternary aminoethyl may be attached to a cross-linked dextran, cellulose, agarose or acrylic support.

The dye-ligand affinity column is used to remove hydrophobic impurities. A typical column comprises a triazinyl dye such as the Red 120 dye Procion Red HE-3B on an agarose support (e.g., Matrex Gel Red A, manufactured by Amicon Corp., Scientific Systems Division, Danvers, Mass.).

Gel filtration is used to separate high and low molecular weight impurities. A particularly useful filtration gel is a cross-linked dextran-based gel, identified by the trademark SEPHADEX G-100, manufactured by Pharmacia Fine Chemicals (Piscataway, N.J.). The resin has a fractionation molecular weight range of 4,000 to 150,000 for globular proteins and peptides and 1,000 to 100,000 polysaccharides. Other commercially available resins having cut-off ranges of from about 1,000 to about 200,000 for proteins may also be used.

Reversed phase chromatography, e.g. fast protein liquid chromatography (FPLC) and high pressure liquid chromatography (HPLC), has been found to be the only procedure capable of removing GM-CSF-related proteins identifiable on electrophoresis with no apparent denaturation of GM-CSF. Any C4 or C8 column may be used, for example, PRORPC-C8 (manufactured by Pharmacia) for FPLC and Dynamax-C4 or Dynamax-C8 (manufactured by Rainin Instruments Co., Woburn, Mass.) for HPLC.

In particular the present invention relates to the purification of proteins having the sequence of the cDNA insert of clone pcD-human-GM-CSF illustrated below, which has been deposited in E. coli with the American Type Culture Collection, Rockville, Md., under accession number 39923.

HUMAN GM-CSF

```
        10          20          30             47
ACACAGAGAG  AAAGGCTAAA  GTTCTCTGGA  GG ATG TGG CTG CAG AGC CTG CTG CTC TTG
                                       MET Trp Leu Gln Ser Leu Leu Leu Leu 62                    77                    92                   107
GGC ACT GTG GCC TGC AGC ATC TCT GCA CCC GCC CGC TCG CCC AGC CCC AGC ACG
Gly Thr Val Ala Cys Ser Ile Ser Ala Pro Ala Arg Ser Pro Ser Pro Ser Thr 122                   137                   152                   167
CAG CCC TGG GAG CAT GTG AAT GCC ATC CAG GAG GCC CGG CGT CTC CTG AAC CTG
Gln Pro Trp Glu His Val Asn Ala Ile Gln Glu Ala Arg Arg Leu Leu Asn Leu 182                   197                   212
AGT AGA GAC ACT GCT GCT GAG ATG AAT GAA ACA GTA GAA GTC ATC TCA GAA ATG
Ser Arg Asp Thr Ala Ala Glu Met Asn Glu Thr Val Glu Val Ile Ser Glu Met 227                   242                   257                   272
TTT GAC CTC CAG GAG CCG ACC TGC CTA CAG ACC CGC CTG GAG CTG TAC AAG CAG
Phe Asp Leu Gln Glu Pro Thr Cys Leu Gln Thr Arg Leu Glu Leu Tyr Lys Gln 287                   302                   317
GGC CTG CGG GGC AGC CTC ACC AAG CTC AAG GGC CCC TTG ACC ATG ATG GCC AGC
Gly Leu Arg Gly Ser Leu Thr Lys Leu Lys Gly Pro Leu Thr Met Met Ala Ser 332                   347                   362                   377
CAC TAC AAG CAG CAC TGC CCT CCA ACC CCG GAA ACT TCC TGT GCA ACC CAG ATT
His Tyr Lys Gln His Cys Pro Pro Thr Pro Glu Thr Ser Cys Ala Thr Gln Ile 392                   407                   422                   437
ATC ACC TTT GAA AGT TTC AAA GAG AAC CTG AAG GAC TTT CTG CTT GTC ATC CCC
Ile Thr Phe Glu Ser Phe Lys Glu Asn Leu Lys Asp Phe Leu Leu Val Ile Pro 452                   467         477         487         497
TTT GAC TGC TGG GAG CCA GTC CAG GAG TGA GACCGGCAG ATGAGGCTGG CCAAGCCGGG
Phe Asp Cys Trp Glu Pro Val Gln Glu  .

507         517         527         537         547         557
GAGCTGCTCT CTCATGAAAC AAGAGCTAGA AACTCAGGAT GGTCATCTTG GAGGGACCAA 567         577         587         597         607         617
GGGGTGGGCC ACAGCCATGG TGGGAGTGGC CAGGACCTGC CCTGGGCACA CTGACCCTGA 627         637         647         657         667         677
TACAGGCATG GCAGAAGAAT GGGAATATTT TATACTGACA GAAATCAGTA ATATTTATAT 687         697         707         717         727         737
ATTTATATTT TTAAAATATT TATTTATTTA TTTATTTAAG TTCATATTCC ATATTTATTC 747         757         767         777         787
AAGATGTTTT ACCGTAATAA TTATTATTAA AAATATGCTT CTAAAAAAAA
```

The following are general aspects of the purification protocol, which is described in more detail in seven stages below:

All operations are performed at 2°–15° C., unless otherwise indicated. Protein concentration is determined at each stage by a Coomassie blue binding assay. pH measurements may vary by ±0.2 pH units and conductivity measurements may vary by ±3 mS. If the expected degree of purification is not achieved in any chromatographic procedure, eluted fractions may be rechromatographed on the same type of column or, alternatively, recycled through a previous step or a previous series of steps. An ammonium sulfate precipitation and/or ultrafiltration step may be performed to concentrate and/or store the protein, as e.g. in Stage III below. All solvents, including those that are employed for either equilibration or elution of columns, are filtered prior to use through a 0.2μ membrane. USP XIX grade water is employed in the preparation of all solvents after Stage IV below.

Stage I. Cell Killing and Protein Extractions

Cells are killed, for example by adjusting to pH 2.0 (or less) by sequential additions of suitable acids, e.g. by adding 85% phosphoric acid to pH 4.5 and 50% trichloroacetic acid to pH 2.0. Substantially all of the suspension liquid is removed from the cells and discarded, a second suspension of the treated cells is prepared, said second suspension is neutralized, and the GM-CSF-containing liquid is separated from the suspended cells, e.g. by filtration through a $0.2\mu$ membrane. The conductivity of the extract is then adjusted to 15–20 mS by addition of water. A low conductivity is required to minimize the amount of dilution required to allow GM-CSF to bind to the QAE column.

Stage II. Quaternary Aminoethyl (QAE) Column Chromatography

If required, the neutralized extract is adjusted to pH 7.5 with sodium hydroxide or hydrochloric acid, as appropriate. The conductivity of the neutralized extract is adjusted to 5–10 mS by addition of deionized water. The QAE column or other suitable anion exchange column is equilibrated with at least 2–3 column volumes of suitable pH 7.5 buffer, e.g. 20 mM Tris-HCl. The extract containing GM-CSF is applied to the column at a loading of not greater than 20 mg per ml of resin. The column is eluted with 10–20 column volumes of a gradient of sodium chloride in the range of 0–0.5M dissolved in the same buffer in which the column was equilibrated. Sodium chloride or other appropriate salt is added to increase the conductivity and thereby elute the GM-CSF. Fractions are combined based on sodium dodecyl sulfate-polyacrylamide gel electrophoresis (SDS-PAGE) and chromatographed in Stage III.

Stage III. Dye Affinity Chromatography

The combined fractions from the anion exchange (e.g. QAE) column are diluted with deionized water to a conductivity of 5–10 mS and loaded onto a dye-ligand affinity column, e.g. Procion Red HE3B attached to an agarose support, which had been previously equilibrated with 2–3 column volumes of appropriate pH 7.5 buffer, e.g. 20 mM Tris-HCl. The amount of protein loaded onto the column should not exceed 10 mg per ml of gel.

The column is washed with 3–4 column volumes of the equilibration buffer. Elution is performed with between 5 and 15 volumes of a gradient of sodium chloride or other appropriate salt from 0 to 0.75M dissolved in the equilibration buffer. The fractions to be employed in Stage IV are combined on the basis of SDS-PAGE.

Stage IV. Concentration By Ultrafiltration and/or Ammonium Sulfate Precipitation If the protein concentration of the combined fractions from the previous stage is less than 1.0 mg/ml, the solution is concentrated by ultrafiltration employing a 3,000–5,000 molecular weight cut-off membrane. The final protein concentration should be 1.0 mg/ml or greater. Ammonium sulfate is added to a final concentration of 60–70%. The precipitate is collected by centrifugation and then washed once with 20 mM Tris-HCl, pH 7.5, or other suitable buffer containing the same concentration of ammonium sulfate as employed for precipitation. The precipitate is collected by centrifugation and dissolved in the same buffer.

Stage V. Gel Filtration Chromatography

The redissolved ammonium sulfate precipitate may be clarified by centrifugation, if required. The solution is filtered through a $0.2\mu$ filter and charged onto a gel filtration column such as a Sephadex G-100 column equilibrated with an appropriate buffer at pH 7.5, e.g. 20 mM Tris-HCl. The amount of protein loaded onto the column should not exceed 3 mg per ml of gel. The column is eluted with the same buffer. Fractions for stage VI are combined based on SDS-PAGE.

Stage VI. Reversed-Phase Column Chromatography

The combined fractions from the gel filtration are passed through a $0.2\mu$ filter and applied to a reversed-phase column, e.g., FPLC or HPLC columns. The column is equilibrated with an acidic solution such as 0.1% trifluoroacetic acid (TFA) and elution is performed with a gradient of 0–100% of an inert solvent such as acetonitrile dissolved in the acidic solution. Fractions are combined based on SDS-PAGE. The solution is lyophilized and the dried powder is dissolved in a buffer solution at pH 7.2, e.g., 20 mM sodium phosphate.

Stage VII. Dialysis of the Purified GM-CSF

The solution from Stage VI is dialyzed against a buffer at pH 7.2, e.g., 20 mM sodium phosphate. Two changes of buffer are performed with a minimum of 4–5 hours between changes. If required, the dialyzed solution is concentrated by ultrafiltration using a 3,000–5,000 molecular weight cut-off membrane to a protein concentration of at least 1.0 mg/ml. The solution of purified GM-CSF is passed through a $0.2\mu$ filter and stored frozen at about $-20°$ C. or below.

Following is a specific example of GM-CSF purification. Roman numerals correspond to some of the Stages of the general description above.

Stage II. QAE Column Chromatography

The neutralized protein extract was adjusted to pH 7.5 with sodium hydroxide. The extract was then diluted approximately 2-fold with cold deionized water to reach a final conductivity of 8 mS. A 6.5 liter column (BIOPROCESS 252/15, manufactured by Pharmacia) was equilibrated with 3 column volumes of 20 mM Tris.HCl, pH 7.5. Extract (50 liters) was applied to the column at a loading of 8.6 mg protein per ml of resin. The column was eluted at a flow of 400 ml/min, first with 30 liters of equilibration buffer, and then with 70 liters of a linear gradient established between 35 liters of 20 mM Tris.HCl, pH 7.5 and 35 liters of 20 mM Tris.HCl, pH 7.5 containing 0.4M NaCl. Fractions (4–5 liters) were combined based on gel electrophoresis (SDS-PAGE) and the pooled protein (2.0 grams) was chromatographed in Stage III.

Stage III. Dye Affinity Chromatography

The combined fractions from the QAE column were concentrated by ultrafiltration (3,000–5,000 molecular weight cut-off membrane) to 1 liter, and then diluted 5-fold with cold deionized water to a conductivity of 8 mS. This pool (5 liters) was then loaded at a ratio of 6.7 mg/ml onto a 300 ml Matrex Gel Red A column which had previously been equilibrated with three column volumes of 20 mM Tris.HCl, pH 7.5. The column was then washed with 600 ml of equilibrating buffer, and the 2.0 gram load was eluted using a linear gradient established between 1.5 liters of 20 mM Tris.HCl, pH 7.5 and 1.5 liters of 20 mM Tris.HCl, pH 7.5 containing 0.75M NaCl. The fractions were combined based on gel electrophoresis, and the fractions (1.5 liters containing 1.12 gram of protein) were concentrated by ultrafiltration in Stage IV.

Stage IV. Concentration of Dye Ligand Eluate By Ultrafiltration

The 1.5 liter eluate of the dye ligand chromatography contained 0.75 mg/ml. Ultrafiltration of this pool was performed in an Amicon high-output stainless steel stirred cell (Model 2000). A YM-5 membrane (150 mm) (Amicon) was used with a flow rate of 10 ml/min., 80 PSI and 4° C. The sample was concentrated to a volume of 75 ml and 10–15 mg/ml. Following the ultrafiltration, the sample was filtered through a 0.22μ cellulose nitrate membrane. Ammonium sulfate was added to a final concentration of 60% (390 mg/ml). The solution was held at 4° C. without mixing for 2 hours, and then centrifuged at 4,000 rpm for 45 min at 4° C. The precipitate was collected, and resuspended in one liter of 20 mM Tris.HCl, pH 7.5 containing 60% saturated ammonium sulfate at 4° C. The sample was centrifuged at 4,000 rpm for 45 min at 4° C.

Stage V. Sephadex G-100 Chromatography

The redissolved ammonium sulfate pellet was charged onto a 2 liter column at a flow rate of 2 ml/min. A loading ratio of 0.5 mg of protein per ml of resin was used and the sample was eluted with the equilibrating buffer, 20 mM Tris.HCl, pH 7.5. Fractions were combined based on gel electrophoresis (SDS-PAGE), and the 300 ml volume containing 350 mg of protein was frozen at −20° C. until it was applied to the reversed-phase column.

Stage VI. Reversed-Phase Column Chromatography

The combined fractions of the gel filtration column were passed through a 0.2μ filter and applied onto a 20 ml PRORPC-C2/C8 (Pharmacia) column at a flow rate of 2.5 ml/min. The column had previously been equilibrated with solvent containing 0.1% TFA in water. Four identical chromatographies (100 mg per run) were performed. Sample was eluted using a linear gradient between 35% acetonitrile, 0.1% TFA and 100% acetonitrile, 0.1% TFA over a 125 min. time period. Fractions were combined based on SDS-PAGE. The solution was lyophilized, and the dried powder was dissolved in 20 mM sodium phosphate, pH 7.2.

Stage VII. Dialysis of The Purified GM-CSF

The pool from the reversed-phase column was dialysed against three changes of 20 mM sodium phosphate buffer, pH 7.2. The solution was then sterile-filtered through a 0.2μ filter and frozen at −20° C.

We claim:

1. A method of purifying granulocyte-macrophage colony-stimulating factor (GM-CSF) from GM-CSF-expressing bacteria comprising:
   (a) killing and disrupting the GM-CSF-expressing bacteria;
   (b) preparing a GM-CSF containing extract from the disrupted GM-CSF-expressing bacteria;
   (c) subjecting the GM-CSF containing extract of step (b) to quarternary amino ethyl (QAE) anion exchange column chromatography to separate proteases from the GM-CSF containing extract thereby producing protease-free GM-CSF containing fractions;
   (d) subjecting the GM-CSF containing fractions obtained from step (c) to red 120 triazinyl dye-ligand affinity column chromatography to produce GM-CSF containing fractions substantially free of hydrophobic impurities;
   (e) subjecting the GM-CSF-containing fractions obtained from step (d) to gel filtration column chromatography to obtain GM-CSF containing fractions substantially free of high and low molecular weight impurities; and
   (f) subjecting the GM-CSF-containing fractions from step (e) to reverse-phase column chromatography so as to obtain fractions containing GM-CSF having a purity greater than 95% homogeneity.

2. A method as claimed in claim 1 wherein the GM-CSF is human GM-CSF.

3. A method as claimed in claim 2 wherein the GM-CSF is recombinant human GM-CSF.

4. The method of claim 1 wherein the reverse-phase column chromatography is carried out by means of either a high pressure liquid chromatography column or a fast protein liquid chromatography column.

5. The method of claim 1 wherein the GM-CSF-expressing bacteria is an E. coli. bacterium.

6. A method for purifying GM-CSF from GM-CSF expressing host cells comprising:
   (a) killing and disrupting the GM-CSF-expressing host cells;
   (b) preparing a GM-CSF containing extract from the disrupted GM-CSF-expressing host cells;
   (c) subjecting the GM-CSF containing extract of step (b) to quaternary amino ethyl (QAE) anion exchange column chromatography to separate proteases from the GM-CSF extract thereby producing protease-free GM-CSF containing fraction(s);
   (d) subjecting the GM-CSF-containing fraction(s) obtained from step
   (c) to red 120 dye-ligand affinity column chromatography to obtain GM-CSF-containing fractions substantially free of hydrophobic impurities; and
   (e) subjecting the GM-CSF containing fractions obtained from step (d) to a gel filtration column, said gel filtration column having a fractionation range from about 1,000 to about 200,000 Daltons to obtain GM-CSF containing fraction(s) substantially free of high and low molecular weight impurities.

* * * * *